United States Patent [19]

Martin et al.

[11] 4,360,668
[45] Nov. 23, 1982

[54] 2-O-METHANESULFONYLFORTIMICIN B

[75] Inventors: Jerry R. Martin; John S. Tadanier, both of Waukegan; Paulette Collum, Zion, all of Ill.

[73] Assignee: Abbott Laboratories, North Chicago, Ill.

[21] Appl. No.: 266,266

[22] Filed: May 22, 1981

Related U.S. Application Data

[62] Division of Ser. No. 91,864, Nov. 6, 1979, Pat. No. 4,276,413, which is a division of Ser. No. 863,006, Dec. 21, 1977, Pat. No. 4,192,867.

[51] Int. Cl.³ .......................................... C07H 15/22
[52] U.S. Cl. .................................................. 536/16.1
[58] Field of Search .................................... 536/17 B

[56] References Cited

U.S. PATENT DOCUMENTS 4,169,198  9/1979  Martin et al. .................... 536/17 R Primary Examiner—Anton H. Sutto
Attorney, Agent, or Firm—Robert L. Niblack; Gildo E. Fato

[57] ABSTRACT

2-Deoxyfortimicin, A, 2-deoxy-4-N-alkyl fortimicins and 2-deoxy-4-N-acyl fortimicins represented by the formula

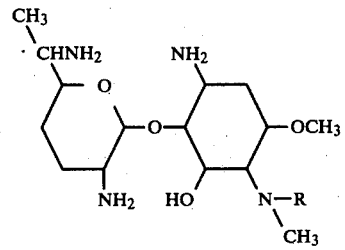

wherein R is selected from the group consisting of acyl, aminoacyl, N-monoloweralkylaminoacyl, N,N-diloweralkylaminoacyl, hydroxy-substituted aminoacyl, an amino acid residue, hydroxyacyl, loweralkyl, aminoloweralkyl, N-monoloweralkylaminoloweralkyl, hydroxyloweralkyl, N-N-diloweralkylaminoloweralkyl or hydroxy-substituted aminoloweralkyl, and the pharmaceutically acceptable salts thereof; intermediates therefor; and pharmaceutical compositions containing the compounds of this invention.

2 Claims, No Drawings

2-O-METHANESULFONYLFORTIMICIN B

This is a division, of application Ser. No. 91,864, now U.S. Pat. No. 4,276,413 filed Nov. 6, 1979, which is a divisional application of 863,006, filed Dec. 21, 1977, now U.S. Pat. No. 4,192,867, issued Mar. 11, 1980.

BACKGROUND OF THE INVENTION

It is known that the anti-bacterial and pharmacological properties of many naturally produced aminoglycoside antibiotics can be altered by structural modifications. For example, certain chemical modifications in the gentamicin and kanamycin family of aminoglycoside antibiotics provide structures which are less toxic than the parent antibiotic. Further, certain chemical modifications in the above family series alter the anti-bacterial spectrum advantageously either by increasing the intrinsic activity or increasing activity against resistant strains.

Recently, a new family of aminoglycoside antibiotics, the fortimicins, have been identified. See U.S. Pat. Nos. 3,976,768 and 3,931,400 which disclose the naturally produced parent antibiotics, Fortimicin A and Fortimicin B. Historically, once an aminoglycoside antibiotic has been in clinical use for awhile, resistant microorganisms arise. In many cases, the resistance is R-factor mediated and is attributed to the ability of the bacteria to enzymatically modify the amino or hydroxyl groups of the aminoglycoside antibiotic. It is known that in the naturally occuring fortimicin aminoglycoside antibiotics blocking the 2-hydroxy group inactivates the antibiotics.

The present invention provides 2-deoxyfortimicin antibiotics and derivatives thereof which have equal in vitro antibacterial activity when compared to the parent fortimicins. The preferred compounds of this invention have equal or increased in vivo activity. In addition, the 2-deoxyfortimicins of this invention cannot be inactivated by R-factor carrying microorganisms which can modify the 2-hydroxyl group of the parent fortimicins.

SUMMARY

2-Deoxyfortimicin A and 2-deoxy-4-N-alkyl and 4-N-acylfortimicin B derivatives are provided by this invention as well as their salts, intermediates useful in the preparation of the compounds of this invention, processes for making the compounds, and compositions employing the antibiotics of this invention as the active component of the composition.

The compounds are administered by parenteral routes of administration in daily dosages of from about 10 to about 200 mg/kg. of body weight daily.

DETAILED DESCRIPTION OF THE INVENTION

This invention provides 2-deoxyfortimicin A and 4-N-alkyl and acyl derivatives of 2-deoxyfortimicin B represented by Formulae I and II, respectively.

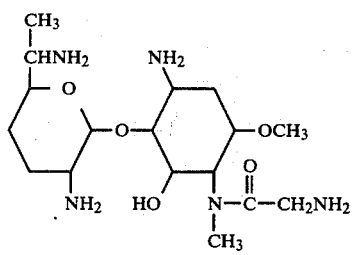

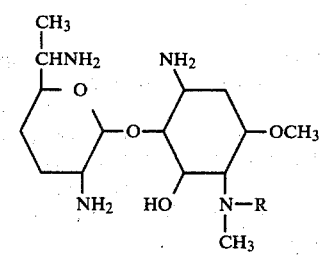

wherein R is selected from the group consisting of acyl, hydroxyacyl, aminoacyl, N-monoloweralkylaminoacyl, N,N-diloweralkylaminoacyl, hydroxyacyl, hydroxy-substituted aminoacyl or an amino acid residue other than glycyl, loweralkyl, aminoloweralkyl, hydroxyloweralkyl, N-monoloweralkylaminoloweralkyl, N,N-diloweralkylaminoloweralkyl or hydroxy-substituted aminoloweralkyl; and the pharmaceutically acceptable salts thereof.

The term "acyl", as used herein, refers to acyl groups represented by the formula $$-\overset{O}{\underset{\|}{C}}-R_1$$

wherin $R_1$ is loweralkyl, i.e., acetyl, propionyl, butyryl, and the like.

The term "an amino acid residue" refers to a D, L or DL amino acid residue such as glycyl, alanyl, sarcosyl, leucyl, isoleucyl, valyl, phenylalanyl, tyrosyl, tryptophyl, seryl, threonyl, methionyl, glutamyl, glutaminyl, aspartyl, asparaginyl, prolyl, histidyl, lysyl, arginyl and the like.

The term "loweralkyl" refers to straight or branched chain alkyl groups having from 1 to 6 carbon atoms, i.e., methyl, ethyl, n-propyl, iso-propyl, n-butyl, sec-butyl, tert-butyl, n-pentyl, n-hexyl, and the like.

The substituted alkyl groups are well known in the art and include, for example, aminomethyl, β-aminoethyl, N-methylaminoethyl, N,N-dimethylaminopropyl, etc.

The term "pharmaceutically acceptable salts" are the non-toxic acid addition salts prepared by reacting the base with a suitable organic or inorganic acid. Representative salts include the hydrochloride, hydrobromide, sulfate, bisulfate, acetate, oxylate, valerate, oleate, palmitate, stearate, laurate borate, benzoate, lactate, phosphate, tosylate, citrate, maleate, fumarate, succinate, tartrate, napsylate and the like.

In addition to the above-described antibiotics of Formulae I and II and their salts, this invention also provides intermediates which are useful in preparing the compounds of Formulae I and II.

The intermediates are represented by the following formulae:

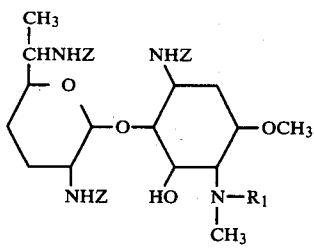

wherein Z is benzyloxycarbonyl and $R_1$ is either hydrogen or glycyl. When $R_1$ is hydrogen, the compound is 1,2',6'-tri-N-benzyloxycrbonyl-2-deoxyfortimicin B. When $R_1$ is glycyl, or N-protected glycyl the compounds are 1,2',6'-tri-N-benzyloxycarbonyl-2-deoxyfortimicin A or 1,2',6'-tri-N-benzyloxycarbonyl-4-N(N-benzyloxycarbonylglycyl)-2-deoxyfortimicin A both of which compounds are key intermediates in preparing the final products of this invention.

Intermediates of Formula IV and V are also provided by the present invention.

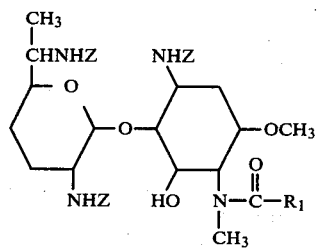

wherein $R_1$ and Z are defined for Formula II; and 4,5-oxazolidines of Formula V:

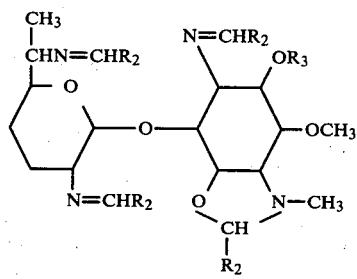

wherein each $R_2$ are the same or different members of the group consisting of hydrogen, aryl or hydroxy, methyl or methoxyl-substituted aryl; and $R_3$ is hydrogen or a $C_1$ to $C_8$ hydrocarbonsulfonic acid such as methanesulfonic acid, ethanesulfonic acid, benzenesulfonic acid, p-toluenesulfonic acid and the like.

Generally speaking, the compound of this invention can be prepared as follows:

In one process, fortimicin B, having all primary amino groups protected by benzyloxycarbonyl groups and the $C_5$ hydroxyl and $C_4$ secondary amino group blocked by a suitable aldehyde to form an oxazolidine ring, upon treatment with a hydrocrbonsulfonyl halide or anhydride, is converted to a 2-O-hydrocarbonsulfonyl ester (e.g., to a 2-O-methanesulfonyl ester) which in turn is converted to a 1,2',6'-tri-N-benzyloxycarbonyl-2-O-hydrocarbonsulfonyl ester derivative, which, following acid hydrolysis of the oxazolidine ring, is N-deblocked by catalytic hydrogenolysis in the presence of an acid. When the resulting 2-O-hydrocarbonsulfonylfortimicin B salt is converted to the free base, the intermediate 1,2-epiminofortimicin B is obtained. Continuing the process, catalytic hydrogenolysis of 1,2-epiminofortimicin B gives 2-deoxyfortimicin B which in turn is converted to the 1,2',6'-tri-N-benzyloxycarbonyl derivative by treatment with a suitable acylating agent such as N-(benzyloxycarbonyloxy)succinimide. The tri-N-benzyloxycarbonyl intermediate is acylated with an activated carboxylic acid derivative to obtain a per-N-blocked 2-deoxy-4-N-acylfortimicin B derivative which is converted to a 2-deoxy-4-N-acylfortimicin B salt by catalytic hydrogenolysis in the present of an acid.

In an alternate procedure, the key intermediate 1,2-epiminofortimicin B, is conveniently prepared as follows. Fortimicin B, having all primary amino groups protected by Shiff base formation from a suitable aldehyde, (e.g. benzaldehyde) and the $C_5$ hydroxyl and $C_4$ secondary amino group protected by the same aldehyde to form an oxazolidine ring, upon treatment with a hydrocarbonsulfonyl halide or anhydride is converted to a 2-O-hydrocarbonsulfonyl ester which in turn is converted on acid hydrolysis of the Schiff base and oxazolidine to a 2-O-hydrocarbonsulfonylfortimicin B salt. The salt, upon conversion to the free base rearranges to 1,2-epiminofortimicin B.

2-Deoxy-4-N-alkylfortimicins B are prepared by treating a per-N-protected-2-deoxy-4-N-acylfortimicin B with a boron hydride reducing agent followed by subsequent removal of the N-protecting groups.

The following examples further illustrate the present invention.

EXAMPLE 1

1,2',6'-Tri-N-benzyloxycarbonylfortimnicin B

To a stirred solution of 2.0 g. of fortimicin B, 30 ml of water and 60 ml of methanol, cooled in an ice bath, is added 4.44 g of N-(benzyloxycarbonyloxy)succinimide. Stirring is continued at 0° for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromatographed on silica gel. Elution with a solvent system composed of chloroform-methanol-concentrated ammonium hydroxide (23.4:1.4:0.1 v/v/v) gives 1.05 g of 1,2',6'-tri-N-benzyloxycarbonylfortimicin B: $[\alpha]_D^{25}+16.5°$ (c 1.0, $CH_3OH$); IR ($CDCl_3$) 1712 and 1507 $cm^{-1}$; NMR ($CDCl_3$) δ 1.03($C_{6'}$—$CH_3$, $J_{6'7'}=6.0$ Hz), 2.32 ($C_4$—$NCH_3$), 3.41 ($OCH_3$).

Anal. Calcd. for $C_{39}H_{50}N_4O_{11}$:C, 62.39;H,6.71; N,7.46. Found: C,62.16; H,6.76; N,7.43.

EXAMPLE 2

1,2',6'-Tri-N-benzyloxycarbonyl-4,5-salicylaldehyde oxazolidine fortimicin B

A solution of 22 g of 1,2',6'-tri-N-benzyloxycarbonyl-fortimicin B in 396 ml of methanol is treated with 3.96 ml of salicylaldehyde and refluxed for 1 hour. Evaporation of the reaction mixture under reduced pressure gives 26 g of 1,2',6'-tri-N-benzyloxycarbonyl-4,5-salicylaldehyde oxazolidine fortimicin B as a brownish yellow solid: NMR ($CDCl_3$) δ 0.94($C_{6'}$—$CH_3$, $J_{6',7'}=7.0$ Hz), 2.34 ($C_4$—$NCH_3$), 3.49 ($C_3$—$OCH_3$), 7.31 (Cbz)

EXAMPLE 3

1,2',6'-Tri-N-benzyloxycarbonyl-4,5-(2-O-methanesulfonylsalicyclaldehyde)-oxazolidine-2-O-methanesulfonylfortimicin B A stirring solution of 26 g of 1,2',6'-tri-N-benzyloxycarbonyl-4,5-salicylaldehyde oxazolidine fortimicin B in 154 ml of dry pyridine is treated with 12.26 ml of freshly distilled methanesulfonylchloride. After stirring for 20 hours, the reaction mixture is poured into 2000 ml of 5% sodium hydrogen carbonate solution and extracted 2 times with 1000 ml portions of chloroform. The combined chloroform extract is washed with 1000 ml of 5% sodium hydrogen carbonate and then twice with 1000 ml portions of water. The chloroform is evaporated under reduced pressure and the pyridine is removed by repeated co-distillation with benzene to give 31.2 g of 1,2',6'-tri-N-benzyloxycarbonyl-4,5-(2-O-methanesulfonylsalicylaldehyde)-oxazolidine-2-O-methanesulfonylfortimicin B: NMR ($CDCl_3$) δ 1.0 ($C_6'$—$CH_3$, $J_{6',7'}=7.0$ Hz), 2.19 ($C_4$—$NCH_3$), 2.94 ($C_2$—$OSO_2CH_3$), 3.15 (Ar—$OSO_2CH_3$), 3.60 ($C_3$—$OCH_3$), 7.33 (Cbz).

EXAMPLE 4

1,2',6'-Tri-N-benzyloxycarbonyl-2-O-methanesulfonylfortimicin B

A stirring solution of 31.2 of 1,2',6'-tri-N-benzyloxycarbonyl-4,5-(2-O-methanesulfonylsalicylaldehyde) oxazolidine-2-O-methanesulfonylfortimicin B in 1000 ml of tetrahydrofuran is treated with 262 ml of 0.4 N hydrochloric acid. After stirring for 4 hours, the reaction mixture is poured into 5700 ml of 6 N ammonium hydroxide solution and extracted 2 times with 1400 ml portions of chloroform. The combined chloroform extract is washed with 5700 ml of 7% sodium hydrogen sulfite solution and then 2 times with 1180 ml portions of water. Removal of the chloroform under reduced pressure gives 27.35 g of crude 1,2',6'-tri-N-benzyloxycarbonyl-2-O-methansulfonylfortimicin B. The crude material is chromatographed on a column (6.0×80 cm) of Sephadex LH-20 gel prepared and eluted with 95% ethanol. Fractions containing the desired material are combined and concentrated to dryness under reduced pressure to give pure 1,2',6'-tri-N-benzyloxycarbonyl-2-O-methanesulfonylfortimicin B as a glass: $[\alpha]_D^{23}+18.5°$ (c 1.0, $CH_3OH$); IR ($CDCl_3$) 3436, 3350, 1703, 1502, 1354 and 1173 $cm^{-1}$; NMR ($CDCl_3$) δ 1.07 ($C_6'$—$CH_3$, $J_{6',7'}=7.0$ Hz), 2.34($C_4$—$NCH_3$), 2.87 ($OSO_2CH_3$), 3.48 ($OCH_3$).

Anal. Calcd. for $C_{40}H_{52}N_4O_{13}S$: C,57.96; H,6.32; N,6.76. Found: C,57.65; H,6.52; N,6.62.

EXAMPLE 5

2-O-Methanesulfonylfortimicin B Tetrahydrochloride

A solution of 4.42 g of 1,2',6'-tri-N-benzyloxycarbonyl-2-O-methanesulfonylfortimicin B in 310 ml of 0.2 N hydrochloric acid in methanol is treated for 4 hours with 4.5 g of 5% palladium on carbon under hydrogen and 3 atmospheres of pressure. The catalyst is filtered off and washed with ethanol. The filtrate is concentrated to dryness under reduced pressure and the excess hydrochloric acid is removed by repeated co-distillation with methanol to leave 2.79 g of 2-O-methanesulfonylfortimicin B tetrahydrochloride as a white glass: $[\alpha]_D^{25}+91.7°$ (c 1.01, $CH_3OH$); IR (KBr) 3400, 2920, 1590, 1330 and 1165 $cm^{-1}$; NMR ($D_2O$) δ 1.82 ($C_6'$—$CH_3$, $J_{6',7'}=7.0$ Hz), 3.31 ($C_4$—$NCH_3$), 3.88 ($C_2OSO_2CH_3$), 4.07 ($_3$—$OCH_3$), 5.88 ($C_1$·H, J=4.0 Hz).

EXAMPLE 6

1,2-Epiminofortimicin B

A solution prepared from 2.8 g of 2-O-methanesulfonylfortimicin B tetrahydrochloride in 20 ml of water is passed through a column (2.2×20 cm) of an anion exchange resin quaternary ammonium styrene type, e.g., AG ® 2-X8, 50–100 mesh resin (OH form) sold by Bio-Rad Laboratories, sufficient to remove the chloride ion. Basic elutes are combined and allowed to stand at room temperature for 72 hours. Evaporation of the water under reduced pressure leaves 3.0 g of 1,2-epiminofortimicin B: NMR ($D_2O$) δ 1.55 ($C_6'$—$CH_3$, $J_{6',7'}=7.0$ Hz), 2.83 $C_4$—$NCH_3$), 4.02 ($C_3$—$OCH_3$), 5.42 ($C_1H, J=3.0$ Hz).

EXAMPLE 7

2-Deoxyfortimicin B and 1-Deamino-2-deoxy-2-epi-aminofortimicin B

A solution prepared from 3.22 g of 1,2-epiminofortimicin B in 250 ml of wet ethanol is treated for 24 hours with 12 g of Raney nickel under 3 atmospheres of hydrogen. The catalyst is collected on a filter and washed with ethanol. The filtrate is concentrated to dryness under pressure to give 2.90 g of a mixture of 2-deoxyfortimicin B and 1-deamino-2-deoxy-2-epi-aminofortimicin B as a white froth. The mixture is chromatographed on a column (2.9×50 cm) of a cation exchange resin, $NH_4^+$ (e.g., Bio-Rad 70, 100–200 mesh, carboxylic styrene type resin sold by Bio-Rad Laboratories) and eluted with a gradient of water to 1 N ammonium hydroxide. The first elutes are taken to dryness under reduced pressure to yield 1.347 g of pure 2-deoxyfortimicin B: NMR ($D_2O$) δ 1.5 ($C_6'$—$CH_3$, $J_{6',7'}=7.0$ Hz), 2.82 ($C_4$—$NCH_3$), 3.86 ($C_3OCH_3$), 5.48 ($C_1,H,J=3.5$ Hz).

Later elutes are collected and taken to dryness under reduced pressure to yield 1.172 g of 1-deamino-2-deoxy-2-epi-aminofortimicin B: NMR ($D_2O$) δ 1.51 ($C_6CH_3$, $J_{6',7'}=7.0$ Hz), 2.83 ($C_4$—$NCH_3$), 4.02 ($C_3$—$OCH_3$), 5.31 ($C_1,H,J=4.0$ Hz).

EXAMPLE 8

1,2',6'-Tri-N-benzyloxycarbonyl-2-deoxyfortimicin B

A stirring, ice-bath cooled solution of 0.843 g of 2-deoxyfortimicin B in 12.6 ml of water and 25.3 ml methanol is treated with 2.09 g of N-(benzyloxycarbonyloxy)succinimide. After stirring in the cold for 3 hours and then at room temperature for 20 hours, the major portion of the methanol is evaporated under reduced pressure. After addition of 90 ml of water, the product is extracted with 180 ml of chloroform. The aqueous portion is extracted 2 more times with 60 ml portions of chloroform. The combined chloroform extract is washed with water and dried over anhydrous magnesium sulfate. Evaporation under reduced pressure gives a foam which is chromatographed on a column (2.3×70 cm) of silica gel prepared and eluted with a solvent system consisting of chloroform-methanol-concentrated ammonium hydroxide (23.4:1.4:0.1 v/v/v). Fractions containing the desired material are collected and evaporated to dryness under reduced pressure to give 0.936 g of 1,2',6'-tri-N-benzyloxycarbonyl-2-deoxyfortimicin B as a colorless froth: NMR (D$_2$O) δ 1.12 (C$_{6'}$, J$_{6',7'}$=6.0 Hz) 2.26 (C$_4$—NCH$_3$), 3.29 (C$_3$—OCH), 4.78 (C$_1$,H, J=4.0 Hz), 7.31 (Cbz).

EXAMPLE 9

Tetra-N-benzyloxycarbonyl-2-deoxyfortimicin A

A stirring solution of 0.807 g of 1,2',6'-tri-N-benzyloxycarbonyl-2-deoxyfortimicin B in 14 ml of dry tetrahydrofuran is treated for 18 hours with 0.439 g of the N-hydroxysuccinimide ester of N-benzyloxycarbonylglycine. The tetrahydrofuran is evaporated under reduced pressure to give 1.231 of colorless froth. The froth is chromatographed on a column (2.0×44 cm) of silica gel prepared and eluted with a solvent system consisting of benzene-methanol-95% ethanol-concentrated ammonium hydroxide (23.5:1.5:1.9:0.2 v/v/v/v). Fractions containing tetra-N-benzyloxycarbonyl-2-deoxyfortimicin A are taken to dryness under reduced pressure and rechromatographed on a column of Sephadex LH-20 prepared and eluted with 95% ethanol. Elutes containing the major product are evaporated to give 0.623 g of tetra-N-benzyloxycarbonyl-2-deoxyfortimicin A: NMR(CDCl$_3$) δ 1.17 (C$_{6'}$—CH$_3$), 2.86 (C$_4$—NCH$_3$), 3.26 (C$_3$—OCH$_3$), 4.83 (C$_1$H, J=4.0 Hz), 7.30(Cbz).

EXAMPLE 10

2-Deoxyfortimicin A Tetrahydrochloride

A solution of 0.463 g of tetra-N-benzyloxycarbonyl-2-deoxyfortimicin A in 60 ml of 0.2 N hydrochloric acid in methanol is treated for 4 hours with 0.463 g of 5% palladium on carbon under 3 atmospheres of hydrogen. The catalyst is collected on a filter and washed with several small portions of methanol. The filtrate is evaporated to dryness under reduced pressure to give a white solid. Excess hydrochloric acid is removed by repeated co-distillation with methanol to leave 0.305 g of 2-deoxyfortimicin A tetrahydrochloride: NMR (D$_2$O) δ 1.79 (C$_{6'}$—CH$_3$, J=7.0 Hz), 3.58 (C$_4$—NCH$_3$), 3.90 (C$_3$—OCH$_3$), 5.82 (C$_1$,H, J=4.0 Hz).

EXAMPLE 11

Tetra-N-benzyloxycarbonyl-2-deoxy-4-N-(β-aminoethyl)fortimicin B

A stirring solution of 1.0 g of tetra-N-benzyloxycarbonyl-2-deoxyfortimicin A in 16 ml of dry tetrahydrofuran purged with nitrogen is treated with 1.0 M diborane (3.0 ml) in tetrahydrofuran. After stirring in a nitrogen atmosphere for 4 hours an additional 2.0 ml of 1.0 M diborane in tetrahydrofuran is added and stirring is continued for another 2 hours. After the cautious addition of water to destroy excess diborane, the reaction mixture is taken to dryness under reduced pressure. Boric acid is removed by repeated co-distillation with methanol to give crude tetra-N-benzyloxycarbonyl-2-deoxy-4-N-(β-aminoethyl)fortimicin B. The crude material is chromatographed on a column of silica gel prepared and eluted with a solvent system consisting of benzene-methanol-95% ethanol-concentrated ammonium hydroxide (23.5:1.5:1.9:0.2 v/v/v/v). Elutes containing the major product are collected and evaporated to dryness to give tetra-N-benzyloxycarbonyl-2-deoxy-4-N-(β-aminoethyl)fortimicin B.

EXAMPLE 12

2-Deoxy-4-N-(β-aminoethyl)fortimicin B pentahydrochloride

A solution prepared from tetra-N-benzyloxycarbonyl-2-deoxy-4-N-(β-aminoethyl)fortimici B and 0.2 N hydrochloric acid in methanol is treated for 4 hours with 5% palladium on carbon under 3 atmospheres of hydrogen. The catalyst, removed by filtration through a celite mat, is washed with additional methanol. The combined filtrates are taken to dryness under reduced pressure to give a white solid. Excess hydrochloric acid is removed by repeated co-distillation with methanol to give 2-deoxy-4-N-(β-aminoethyl)fortimicin B pentahydrochloride.

EXAMPLE 13

1,2',6'-Tri-N-Salicylidene-4,5-Salicylaldehyde Oxazolidine Fortimicin B

A solution of 2.0 g of fortimicin B in 16 ml of methanol is treated with 0.24 ml of salicylaldehyde and refluxed for 1 hour. Evaporation of the reaction mixture under reduced pressure gives 4.563 g of 1,2',6'-tri-N-salicylidene-4-5-salicylaldehyde oxazolidine fortimicin B as a froth: NMR (CDCl$_3$) δ 1.09 (C$_{6'}$—CH$_3$), 2.37 (C$_4$—NCH$_3$), 3.5 (C$_3$—OCH$_3$), 5.24 (C$_1$, H), 8.14, 8.28, 8.40 (—N═CH—C$_6$H$_6$O).

EXAMPLE 14

1,2',6'-Tri-N-(2-O-methanesulfonylsalicylidene)-4,5-(2-O-methanesulfonylsalicylaldehyde)-oxazolidine-2-O-methanesulfonylfortimicin B A stirring solution of 1.0 g of 1,2',6'-tri-N-salicylidene-4,5-salicylaldehyde oxazolidine fortimicin B in 5.9 ml of dry pyridine is treated with 0.6 ml of freshly distilled methanesulfonylchloride. After stirring for 3 hours the reaction mixture is poured into 100 ml of 5% sodium hydrogen carbonate solution. The solution is extracted 2 times with 50 ml portions of chloroform. The combined chloroform extract is washed with 50 ml of 5% sodium hydrogen carbonate solution and then 2 times with 25 ml portions of water. The chloroform is evaporated under reduced pressure and the residual pyridine is removed by repeated co-distillation with benzene to give 1.349 g of 1,2',6'-tri-N-(2-O-methanesulfonylsalicylidene)-4,5-(2-O-methanesulfonylsalicylaldehyde)-oxazolidine-2-O-methanesulfonylfortimicin B: NMR (CDCl$_3$) δ 0.98 (C$_{6'}$—CH$_3$), 7.18 (C$_4$—NCH$_3$).

EXAMPLE 15

2-O-Methanesulfonylfortimicin B Tetrahydrochloride

A stirring solution of 1.34 g of 1,2',6'-tri-N-(2-O-methanesulfonylsalicylidene)-4,5-(2-O-methanesulfonylsalicylaldehyde)-oxazolidine-2-O-methanesulfonylfortimicin B in 44 ml of tetrahydrofuran is treated with 11.1 ml of 0.4 N hydrochloric acid. After stirring for 4 hours the reaction mixture is extracted 3 times with 50 ml portions of chloroform which are discarded. The aqueous layer is taken to dryness to give 0.556 g of 2-O-methanesulfonylfortimicin B tetrahydrochloride.

EXAMPLE 16

In Vitro Antibiotic Activities of 2-Deoxyfortimicins

The in vitro antibiotic activities are determined by a two-fold dilution test using Mueller-Hinton agar, 10 ml per Petri plate. The inoculum of approximately 1×10$^5$ of the indicated test organism is delivered by the Steer's replicator. The test is incubated at 37° C. for 24 hours. Fortimicin A tetrahydrochloride and fortimicin A disulfate are used as the control antibiotics. The minimum inhibitory concentrations (MIC), listed in Table I, are expressed in mcg/ml.

TABLE I

In Vitro Antimicrobial Activity of 2-Deoxyfortimicin A.4 HCl

| Microorganism | Minimum inhibitory concentration (mcg/ml) | | |
|---|---|---|---|
| | Fortimicin A di-Sulfate | Fortimicin A tetra-hydro-chloride | 2-deoxy-forti-micin A tetrahydro-chloride |
| Staph. aureus Smith | 0.78 | 0.78 | 0.78 |
| Strep. faecalis 10541 | 50 | 50 | 50 |
| Enterobacter aerogenes 13048 | 3.1 | 3.1 | 3.1 |
| E. coli Juhl | 6.2 | 6.2 | 6.2 |
| E. coli BL 3676 (Res) | 25 | 25 | 25 |
| Kleb. pneumoniae 10031 | 3.1 | 1.56 | 1.56 |
| Kleb. pneumoniae KY 4262 | 6.2 | 3.1 | 6.2 |
| Providencia 1577 | 3.1 | 3.1 | 3.1 |
| Pseudo. aeruginosa BMH #10 | 0.78 | 0.78 | 0.78 |
| Pseudo aeruginosa KY 8512 | 12.5 | 25 | 12.5 |
| Pseudo. aeruginosa KY 8516 | 50 | 100 | 50 |
| Psuedo. aeruginosa 209 | >100 | >100 | >100 |
| Psuedo. aeruginosa 27853 | 12.5 | 25 | 12.5 |
| Sal. typhimurium Ed. #9 | 1.56 | 1.56 | 1.56 |
| Serratis marcescens 4003 | 1.56 | 3.1 | 3.1 |
| Shigella sonnei 9290 | 6.2 | 12.5 | 6.2 |
| Proteus rettigeri U6333 | 12.5 | 25 | 25 |
| Proteus vulgaris JJ | 6.2 | 6.2 | 3.1 |
| Proteus mirabilis Fin. #9 | 6.2 | 6.2 | 6.2 |
| E. coli 76-2 | 6.2 | 3.1 | 3.1 |

EXAMPLE 17

Acute Mouse Protection Activity of 2-Deoxyfortimicin A

The acute mouse protection activity of 2-deoxyfortimicin A tetrahydrochloride is shown in Table II.

The actue mouse protection test is conducted on 10 mice with each of 5 levels of drug. Mouse mortality is used to calculate a $ED_{50}$ value, i.e., dose of drug required to protect 50% of the test animals.

The actue mouse protection test is conducted on female, swiss albino mice, 18–20 grams in weight. The mice are injected intraperitoneally with an 18 hour culture of the indicated test organism diluted sufficiently to provide the desired $LD_{50}$ value. To check potency of the infection a titration of the indicated test organism is carried out in control animals. The treatment group of animals is dosed with the test fortimicin at one and five hours post-infection and observed for seven days. The $ED_{50}$ values are calculated using the mortality data collected.

TABLE II

Acute Mouse Protection Activity

| Microorganism | Antibiotic | Effective Dose$_{50}$ ($ED_{50}$) (mg/kg) |
|---|---|---|
| Escherichia coli (Juhl) | 2-deoxyfortimicin A tetrahydrochloride | 4.7 |
| | fortimicin A di-sulfate | 4.6 |
| Klebsiella pneumoniae (4508) | 2-deoxyfortimicin A tetrahydrochloride | 1.5 |
| | fortimicin A di-sulfate | 2.5 |
| Proteus mirabilis (Fin 9) | 2-deoxyfortimicin A tetrahydrochloride | 4.7 |
| | fortimicin A di-sulfate | 7.5 |

The compounds of this invention are active as systemic antibiotics when injected by parenteral routes of administration, i.e., by the intramuscular, intravenous, intraparitoneal or subcutaneous routes of administration. The compounds can also be administered orally in those instances where it is desirable to sterilize the intestinal tract and can additionally be applied topically or rectally.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized, by for example, filtration through a bacteria-retaining filter, by incorporating sterilizing agents into the compositions. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 10 to 200 mg/kg of body weight daily are administered to a mammalian patient suffering from an infection caused by susceptible organism.

We claim:
1. 2-O-methanesulfonylfortimicin B or a pharmaceutically acceptable salt thereof.
2. The tetrahydrochloride salt of the compound of claim 1.

* * * * *